US012758621B2

(12) United States Patent
He

(10) Patent No.: US 12,758,621 B2
(45) Date of Patent: *Oct. 13, 2026

(54) ANTIVIRAL ANIMAL FEED ADDITIVE

(71) Applicant: Changde Jizhi Biological Technology Co., Ltd, Changde (CN)

(72) Inventor: Xinqiao He, Changde (CN)

(73) Assignee: Changde Jizhi Biological Technology Co., Ltd., Changde (CN)

( * ) Notice: Subject to any disclaimer, the term of this patent is extended or adjusted under 35 U.S.C. 154(b) by 323 days.

This patent is subject to a terminal disclaimer.

(21) Appl. No.: 18/534,572

(22) Filed: Dec. 9, 2023

(65) Prior Publication Data

US 2025/0186560 A1 Jun. 12, 2025

(51) Int. Cl.

| | |
|---|---|
| ***A61K 38/43*** | (2006.01) |
| ***A23K 20/189*** | (2016.01) |
| ***A61K 36/28*** | (2006.01) |
| ***C12N 9/98*** | (2006.01) |

(52) U.S. Cl.

CPC ............ *A61K 38/43* (2013.01); *A23K 20/189* (2016.05); *A61K 36/28* (2013.01); *C12N 9/98* (2013.01); *A61K 2300/00* (2013.01)

(58) Field of Classification Search

CPC ........ A61K 36/03; A61K 36/10; A61K 36/28; A61K 36/282; A61K 36/35; A61K 36/484; A61K 36/534; A61K 36/57; A61K 36/8962; A61K 33/04; A61K 33/42; A61K 38/43

See application file for complete search history.

(56) References Cited

FOREIGN PATENT DOCUMENTS

| | | | | | |
|---|---|---|---|---|---|
| CN | 104547174 | B | * | 3/2017 | |
| CN | 112956588 | A | * | 6/2021 | ............. A23K 10/30 |
| CN | 114470148 | A | * | 5/2022 | ........... A61K 31/715 |

OTHER PUBLICATIONS https://en.wikipedia.org/wiki/Lonicera_japonica (Year: 2026).*
https://olimp-labs.pl/produkty/garlicin/?lang=en#:~:text=Product%20description,level%20and%20blood%20lipid%20level. (Year: 2026).*
U.S. Appl. No. 18/534,574 (Year: 2023).*
CN104547174B English Translation (Year: 2015).*
CN112956588A—English Translation (Year: 2021).*
CN114470148A—English Translation (Year: 2022).*

* cited by examiner

*Primary Examiner* — Ruth A Davis
(74) *Attorney, Agent, or Firm* — Hemisphere Law, PLLC

(57) ABSTRACT

An antiviral animal feed additive is an enzyme and is made from the following ingredients: *Artemisia argyi, Lactuca sativa, Allium tuberosum, Allium cepiforme, Litsea* rubescensLeeomte, *Glycyrrhiza uralensis, Allium sativum, Mentha canadensis, Allium mongolicum, Lonicera japonica, Sargassum*, monazite, calcium carbonate, fructo-oligosaccharide (FOS), isomaltooligosaccharide (IMO), and organic selenium. The antiviral animal feed additive can be used to prevent from influenza A virus H1N1 and its complications, and has been performed effectiveness and safety tests in a virus research institute, indicating that the antiviral animal feed additive does not damage animal cells. Moreover, the enzyme is added into animal feed to achieve a good antiviral effect.

5 Claims, No Drawings

ANTIVIRAL ANIMAL FEED ADDITIVE

TECHNICAL FIELD

The disclosure relates to the technical field of biotechnology, particularly to an antiviral animal feed additive.

BACKGROUND

Feed additives are added into animal feed in a small amount or a trace amount during processing the animal feed as well as using the animal feed. Although the amount of the feed additives is small, the feed additives still have a significant influence on the animal feed. The feed additives are inevitable ingredients used in modern feed industry, which have significant effects on enhancing nutritional values of the conventional animal feed, improving animal performance, ensuring animal health, saving feed costs, and improving the quality of livestock products.

Enzymes are widely stored in organisms and participate in various physiological functions such as metabolism. Among the enzymes, antimicrobial enzymes are capable of hydrolyzing cell walls of microbes. For example, lysozyme can dissolve the cell walls of microbes to kill the microbes. Moreover, the lysozyme is abundant in saliva, tears, milk, and body tissues of humans and animals, and is an important non-specific immune factor for humans and animals. Therefore, the lysozyme and the health of humans and animals are closely bound up.

Compared with a traditional antibiotic, bacteriolysis (also referred to as bactericidal effect) of the lysozyme is capable of fighting against all of serotypes of a certain pathogenic bacterium, thereby overcoming a deficiency that each antibiotic can only fight against the certain pathogenic bacterium or fight against a certain serotype among all of the serotypes of the certain pathogenic bacterium. Furthermore, the lysozyme has no issues with drug residue and resistance. The lysozyme not only dissolves (kills) the bacterium, enhances animal immunity, but also binds with a virus to inactivate the virus. As a feed additive in livestock and poultry, as well as aquatic products industry, the lysozyme is a good choice in replacing antibiotics, controlling drug-resistant bacteria, and producing green food such as meat, eggs, and dairy products.

However, with the spread of diseases such as avian influenza and African swine fever, there are new requirements for the animal feed. Specially, there is an urgent need to add antiviral ingredients in the animal feed, which is also of great significance in animal husbandry.

SUMMARY

An objective of the disclosure is to provide an antiviral animal feed additive, which is an enzyme. The enzyme can generate some active substances, including amino acids, peptides, vitamins, polysaccharides, polyphenols, flavonoid, alcohols, esters, enzymes, minerals, organic acids, and various probiotics. Therefore, the antiviral animal feed additive is capable of dissolving a protein shell of a virus, as well as possesses performances of deodorization, air purification, water purification, and antibacterial and antimicrobial properties.

Compared with the related art, a technical solution of the disclosure is as follows.

An antiviral animal feed additive is provided by the disclosure, which is an enzyme (also referred to as a toxin-dissolving biomimetic enzyme); and the enzyme is made from the following ingredients:

300 grams (g) to 500 g of *Artemisia argyi,* 200 g to 300 g of *Lactuca sativa,* 200 g to 300 g of *Allium tuberosum,* 300 g to 400 g of *Allium cepiforme,* 200 g to 300 g of *Litsea* rubescensLeeomte, 50 g to 150 g of *Glycyrrhiza uralensis,* 50 g to 150 g of *Allium sativum,* 75 g to 150 g of *Mentha canadensis,* 100 g to 200 g of *Allium mongolicum,* 50 g to 150 g of *Lonicera japonica,* 80 g to 120 g of *Sargassum,* 20 g to 30 g of monazite, 25 g to 35 g of calcium carbonate, 10 g to 20 g of fructo-oligosaccharide (FOS), 8 g to 12 g of isomaltooligosaccharide (IMO), and 20 g to 40 g of organic selenium.

In an embodiment, a weight percentage of the toxin-dissolving biomimetic enzyme in animal feed is in a range of 0.2%-1.0%.

In an embodiment, a weight percentage of the toxin-dissolving biomimetic enzyme in the animal feed is in a range of 0.4%-0.8%.

In an embodiment, a weight percentage of the toxin-dissolving biomimetic enzyme in the animal feed is 0.5%.

In an embodiment, the enzyme is made from the following ingredients:

300 g of the *Artemisia argyi,* 200 g of the *Lactuca sativa,* 200 g of the *Allium tuberosum,* 300 g of the *Allium cepiforme,* 200 g of the *Litsea* rubescensLeeomte, 50 g of the *Glycyrrhiza uralensis,* 50 g of the *Allium sativum,* 75 g of the *Mentha canadensis,* 100 g of the *Allium mongolicum,* 50 g of the *Lonicera japonica,* 80 g of the *Sargassum,* 20 g of the monazite, 25 g of the calcium carbonate, 10 g of the FOS, 8 g of the IMO, and 20 g of the organic selenium.

In an embodiment, the enzyme is made from the following ingredients:

500 g of the *Artemisia argyi,* 300 g of the *Lactuca sativa,* 300 g of the *Allium tuberosum,* 400 g of the *Allium cepiforme,* 300 g of the *Litsea* rubescensLeeomte, 150 g of the *Glycyrrhiza uralensis,* 100 g of the *Allium sativum,* 150 g of the *Mentha canadensis,* 200 g of the *Allium mongolicum,* 150 g of the *Lonicera japonica,* 120 g of the *Sargassum,* 30 g of the monazite, 35 g of the calcium carbonate, 20 g of the FOS, 12 g of the IMO, and 40 g of the organic selenium.

In an embodiment, the enzyme is prepared by the following steps:

step 1, drying the *Lactuca sativa*, the *Allium tuberosum*, the *Litsea* rubescensLeeomte, the *Glycyrrhiza uralensis*, the *Allium mongolicum*, and the *Lonicera japonica* individually according to their weight to obtain dried materials, grinding the dried materials in a grinder to obtain grinded materials, decocting the grinded materials by using purified water to obtain decoction, and then filtering the decoction to obtain a slurry (i.e., thickened liquid); soaking the *Artemisia argyi* and the *Mentha canadensis* into water for 1 hour (h) to obtain soaked materials, distilling the soaked materials by a steam distillation method to obtain a distilled product, and then adding the distilled product into water to perform a time of extraction by reducing pressure to obtain an extracted product, filtering and concentrating the extracted product to a target relative density, thereby obtaining a medicinal liquid 1 for later use; and crushing the *Allium sativum* and the *Allium cepiforme* to obtain crushed materials, adding the crushed materials into water to perform a warm infusion for 3 h in a hermetic environment to obtain an infused mixture, adding ethanol into the infused mixture until a concentration of the ethanol is 50%, thereafter performing an extraction by reducing pressure to obtain a product, filtering and concentrating the product to a target relative density, thereby obtaining a medicinal liquid 2;

step 2, adding the medicinal liquid 1, the medicinal liquid 2, and the slurry into a material mixing tank and then stirring evenly to obtain a mixed liquid;

step 3, adding the *Sargassum* into the mixed liquid obtained in the step 2, and stewing the mixed liquid added with the *Sargassum* to obtain a stewed product, taking out the stewed product to filter and cool down to obtain a cooled mixed liquid;

step 4, adding 20% of the weight of the FOS and 20% of the weight of the IMO into the cooled mixed liquid obtained in the step 3, and then stirring uniformly, and placing the cooled mixed liquid added with the FOS and the IMO into a fermentation tank for a first fermentation to obtain a first fermentation broth; taking out and filtering the first fermentation broth to obtain a filtered first fermentation broth, adding the remained FOS and the remained IMO into the filtered first fermentation broth, and then placing the filtered first fermentation broth added with the remained FOS and the remained IMO into the fermentation tank for a second fermentation to obtain a second fermentation broth;

step 5, crushing the monazite and the calcium carbonate to obtain mixed powder; placing the mixed powder into a furnace with a temperature of 2,000-2,200 degrees Celsius (° C.) and then sintering for 75-105 minutes (min) to obtain sintered powder; cooling the sintered powder to obtain cooled powder, placing the cooled powder into a cloth bag with 800-1,200 meshes and then distilling the cooled powder with a steamer to obtain a distilled liquid for later use; and step 6, distilling the second fermentation broth obtained in the step 4 until there is no distillate to obtain a distilled fermentation broth for later use; mixing the distilled fermentation broth, the distilled liquid obtained in the step 5, and the organic selenium completely to obtain a mixed liquid; adding the mixed liquid into olive oil according to a volume ratio of the mixed liquid to the olive oil of 1:5-10, thereby obtaining the enzyme.

In an embodiment, the animal feed is antiviral.

In an embodiment, an application method of the antiviral animal feed additive includes: adding the antiviral animal feed additive into the animal feed to feed animals.

The disclosure further provides a composite, used to prepare an antiviral animal feed additive; and the composite includes the following materials:

300 g to 500 g of *Artemisia argyi,* 200 g to 300 g of *Lactuca sativa,* 200 g to 300 g of *Allium tuberosum,* 300 g to 400 g of *Allium cepiforme,* 200 g to 300 g of *Litsea* rubescensLeeomte, 50 g to 150 g of *Glycyrrhiza uralensis,* 50 g to 150 g of *Allium sativum,* 75 g to 150 g of *Mentha canadensis,* 100 g to 200 g of *Allium mongolicum,* 50 g to 150 g of *Lonicera japonica,* 80 g to 120 g of *Sargassum,* 20 g to 30 g of monazite, 25 g to 35 g of calcium carbonate, 10 g to 20 g of FOS, 8 g to 12 g of IMO, and 20 g to 40 g of organic selenium.

Beneficial effects of the disclosure are follows.

The disclosure includes the *Artemisia argyi*, the *Lactuca sativa*, the *Allium tuberosum*, the *Allium cepiforme*, the *Litsea* rubescensLeeomte, the *Glycyrrhiza uralensis*, the *Sargassum*, the monazite, the calcium carbonate, the FOS, and the IMO, and the prepared antiviral animal feed additive can achieve a good antiviral effect. The organic selenium described in the disclosure is one of selenium enriched yeast, kappa-selenocarrageenan, selenium enriched *Capsella bursa-pastoris* powder extract, selenium enriched *Cardamine occulta* powder extract, selenium enriched *Brassica rapa* powder extract, selenium enriched *Brassica oleracea* powder extract, and selenium enriched *Fructus Hordei germinatus* powder extract.

DETAILED DESCRIPTION OF EMBODIMENTS

In order to facilitate a better understanding of the disclosure by those skilled in the related art, the following is a clear and complete description of the technical solution in embodiments of the disclosure. Apparently, the described embodiments are only a part of the embodiments of the disclosure, not all of the embodiments of the disclosure. Based on the embodiments in the disclosure, all of other embodiments obtained by those skilled in the related art without creative labor shall fall within the scope of the protection of the disclosure.

Embodiment 1

An enzyme for killing viruses (also referred to as an enzyme, i.e., an antiviral animal feed additive) and a preparation method thereof are provided. Specially, the enzyme is made from the following ingredients:

300 g of *Artemisia argyi,* 200 g of *Lactuca sativa,* 200 g of *Allium tuberosum,* 300 g of *Allium cepiforme,* 200 g of *Litsea* rubescensLeeomte, 50 g of *Glycyrrhiza uralensis,* 50 g of *Allium sativum,* 75 g of *Mentha canadensis,* 100 g of *Allium mongolicum,* 50 g of *Lonicera japonica,* 80 g of *Sargassum,* 20 g of monazite, 25 g of calcium carbonate, 10 g of fructo-oligosaccharide (FOS), 8 g of isomaltooligosaccharide (IMO), and 20 g of organic selenium.

The preparation method of the enzyme in the embodiment 1 is as follows:

step 1, drying the *Lactuca sativa*, the *Allium tuberosum*, the *Litsea* rubescensLeeomte, the *Glycyrrhiza uralensis*, the *Allium mongolicum*, and the *Lonicera japonica* individually according to their weight to obtain dried materials, grinding the dried materials in a grinder to obtain grinded materials, decocting the grinded materials by using purified water to obtain decoction, and then filtering the decoction to obtain a slurry; soaking the *Artemisia argyi* and the *Mentha canadensis* into water for 1 hour (h) to obtain soaked materials, distilling the soaked materials by a steam distillation method to obtain a distilled product, and then adding the distilled product into water to perform a time of extraction by reducing pressure to obtain an extracted product, filtering and concentrating the extracted product to a target relative density, thereby obtaining a medicinal liquid 1 for later use; and crushing the *Allium sativum* and the *Allium cepiforme* to obtain crushed materials, adding the crushed materials into water to perform a warm infusion for 3 h in a hermetic environment to obtain an infused mixture, adding ethanol into the infused mixture until a concentration of the ethanol is 50%, thereafter performing an extraction by reducing pressure to obtain a product, filtering and concentrating the product to a target relative density, thereby obtaining a medicinal liquid 2;

step 2, adding the medicinal liquid 1, the medicinal liquid 2, and the slurry into a material mixing tank and then stirring evenly to obtain a mixed liquid;

step 3, adding the *Sargassum* into the mixed liquid obtained in the step 2, and stewing the mixed liquid added with the *Sargassum* to obtain a stewed product, taking out the stewed product to filter and cool down to obtain a cooled mixed liquid;

step 4, adding 20% of the weight of the FOS and 20% of the weight of the IMO into the cooled mixed liquid obtained in the step 3, and then stirring uniformly, and placing the cooled mixed liquid added with the FOS and the IMO into a fermentation tank for a first fermentation to obtain a first fermentation broth; taking out and filtering the first fermentation broth to obtain a filtered first fermentation broth, adding the remained FOS and the remained IMO into the filtered first fermentation broth, and then placing the filtered first fermentation broth added with the remained FOS and the remained IMO into the fermentation tank for a second fermentation to obtain a second fermentation broth;

step 5, crushing the monazite and the calcium carbonate to obtain mixed powder; placing the mixed powder into a furnace with a temperature of 2,000 degrees Celsius (° C.), and then sintering for 105 minutes (min) to obtain sintered powder; cooling the sintered powder to obtain cooled powder, placing the cooled powder into a cloth bag with 800 meshes and then distilling the cooled powder with a steamer to obtain a distilled liquid for later use; and step 6, distilling the second fermentation broth obtained in the step 4 until there is no distillate to obtain a distilled fermentation broth for later use; mixing the distilled fermentation broth, the distilled liquid obtained in the step 5, and the organic selenium completely to obtain a mixed liquid; adding the mixed liquid into olive oil according to a volume ratio of the mixed liquid to the olive oil of 1:5, thereby obtaining the enzyme.

Embodiment 2

An enzyme for killing viruses and a preparation method thereof are provided. Specially, the enzyme is made from the following ingredients:

500 g of *Artemisia argyi,* 300 g of *Lactuca sativa,* 300 g of *Allium tuberosum,* 400 g of *Allium cepiforme,* 300 g of *Litsea* rubescensLeeomte, 150 g of *Glycyrrhiza uralensis,* 100 g of *Allium sativum,* 150 g of *Mentha canadensis,* 200 g of *Allium mongolicum,* 150 g of *Lonicera japonica,* 120 g of *Sargassum,* 30 g of monazite, 35 g of calcium carbonate, 20 g of FOS, 12 g of IMO, and 40 g of organic selenium.

The preparation method of the enzyme in the embodiment 2 is as follows:

step 1, drying the *Lactuca sativa*, the *Allium tuberosum*, the *Litsea* rubescensLeeomte, the *Glycyrrhiza uralensis*, the *Allium mongolicum*, and the *Lonicera japonica* individually according to their weight to obtain dried materials, grinding the dried materials in a grinder to obtain grinded materials, decocting the grinded materials by using purified water to obtain decoction, and then filtering the decoction to obtain a slurry; soaking the *Artemisia argyi* and the *Mentha canadensis* into water for 1 h to obtain soaked materials, distilling the soaked materials by a steam distillation method to obtain a distilled product, and then adding the distilled product into water to perform a time of extraction by reducing pressure to obtain an extracted product, filtering and concentrating the extracted product to a target relative density, thereby obtaining a medicinal liquid 1 for later use; and crushing the *Allium sativum* and the *Allium cepiforme* to obtain crushed materials, adding the crushed materials into water to perform a warm infusion for 3 h in a hermetic environment to obtain an infused mixture, adding ethanol into the infused mixture until a concentration of the ethanol is 50%, thereafter performing an extraction by reducing pressure to obtain a product, filtering and concentrating the product to a target relative density, thereby obtaining a medicinal liquid 2;

step 2, adding the medicinal liquid 1, the medicinal liquid 2, and the slurry into a material mixing tank and then stirring evenly to obtain a mixed liquid;

step 3, adding the *Sargassum* into the mixed liquid obtained in the step 2, and stewing the mixed liquid added with the *Sargassum* to obtain a stewed product, taking out the stewed product to filter and cool down to obtain a cooled mixed liquid;

step 4, adding 20% of the weight of the FOS and 20% of the weight of the IMO into the cooled mixed liquid obtained in the step 3, and then stirring uniformly, and placing the cooled mixed liquid added with the FOS and the IMO into a fermentation tank for a first fermentation to obtain a first fermentation broth; taking out and filtering the first fermentation broth to obtain a filtered first fermentation broth, adding the remained FOS and the remained IMO into the filtered first fermentation broth, and then placing the filtered first fermentation broth added with the remained FOS and the remained IMO into the fermentation tank for a second fermentation to obtain a second fermentation broth;

step 5, crushing the monazite and the calcium carbonate to obtain mixed powder; placing the mixed powder into a furnace with a temperature of 2,200° C. and then sintering for 75 min to obtain sintered powder; cooling the sintered powder to obtain cooled powder, placing the cooled powder into a cloth bag with 1,200 meshes and then distilling the cooled powder with a steamer to obtain a distilled liquid for later use; and step 6, distilling the second fermentation broth obtained in the step 4 until there is no distillate to obtain a distilled fermentation broth for later use; mixing the distilled fermentation broth, the distilled liquid obtained in the step 5, and the organic selenium completely to obtain a mixed liquid; adding the mixed liquid into olive oil according to a volume ratio of the mixed liquid to the olive oil of 1:10, thereby obtaining the enzyme.

Comparative Example 1

An enzyme for killing viruses and a preparation method thereof are provided. Specially, the enzyme is made from the following ingredients:

200 g of *Allium tuberosum,* 200 g of *Litsea* rubescensLeeomte, 50 g of *Glycyrrhiza uralensis,* 50 g of *Allium sativum,* 75 g of *Mentha canadensis,* 100 g of *Allium mongolicum,* 50 g of *Lonicera japonica,* 80 g of *Sargassum,* 20 g of monazite, 25 g of calcium carbonate, 10 g of FOS, 8 g of IMO, and 20 g of organic selenium.

The preparation method of the enzyme in the comparative example 1 is as follows:

step 1, drying the *Allium tuberosum*, the *Litsea* rubescensLeeomte, the *Glycyrrhiza uralensis*, the *Allium mongolicum*, and the *Lonicera japonica* individually according to their weight to obtain dried materials, grinding the dried materials in a grinder to obtain grinded materials, decocting the grinded materials by using purified water to obtain decoction, and then filtering the decoction to obtain a slurry; soaking the *Mentha canadensis* into water for 1 h to obtain a soaked material, distilling the soaked material by a steam distillation method to obtain a distilled product, and then adding the distilled product into water to perform a time of extraction by reducing pressure to obtain an extracted product, filtering and concentrating the extracted product to a target relative density, thereby obtaining a medicinal liquid 1 for later use; and crushing the *Allium sativum* to obtain a crushed material, adding the crushed material into water to perform a warm infusion for 3 h in a hermetic environment to obtain an infused mixture, adding ethanol into the infused mixture until a concentration of the ethanol is 50%, thereafter performing an extraction by reducing pressure to obtain a product, filtering and concentrating the product to a target relative density, thereby obtaining a medicinal liquid 2;

step 2, adding the medicinal liquid 1, the medicinal liquid 2, and the slurry into a material mixing tank and then stirring evenly to obtain a mixed liquid;

step 3, adding the *Sargassum* into the mixed liquid obtained in the step 2, and stewing the mixed liquid added with the *Sargassum* to obtain a stewed product, taking out the stewed product to filter and cool down to obtain a cooled mixed liquid;

step 4, adding 20% of the weight of the FOS and 20% of the weight of the IMO into the cooled mixed liquid obtained in the step 3, and then stirring uniformly, and placing the cooled mixed liquid added with the FOS and the IMO into a fermentation tank for a first fermentation to obtain a first fermentation broth; taking out and filtering the first fermentation broth to obtain a filtered first fermentation broth, adding the remained FOS and the remained IMO into the filtered first fermentation broth, and then placing the filtered first fermentation broth added with the remained FOS and the remained IMO into the fermentation tank for a second fermentation to obtain a second fermentation broth;

step 5, crushing the monazite and the calcium carbonate to obtain mixed powder; placing the mixed powder into a furnace with a temperature of 2,000° C. and then sintering for 105 min to obtain sintered powder; cooling the sintered powder to obtain cooled powder, placing the cooled powder into a cloth bag with 800 meshes and then distilling the cooled powder with a steamer to obtain a distilled liquid for later use; and step 6, distilling the second fermentation broth obtained in the step 4 until there is no distillate to obtain a distilled fermentation broth for later use; mixing the distilled fermentation broth, the distilled liquid obtained in the step 5, and the organic selenium completely to obtain a mixed liquid; adding the mixed liquid into olive oil according to a volume ratio of the mixed liquid to the olive oil of 1:5, thereby obtaining the enzyme.

Comparative Example 2

An enzyme for killing viruses and a preparation method thereof are provided. Specially, the enzyme is made from the following ingredients:

500 g of *Artemisia argyi,* 300 g of *Lactuca sativa,* 300 g of *Allium tuberosum,* 400 g of *Allium cepiforme,* 300 g of *Litsea* rubescensLeeomte, 150 g of *Glycyrrhiza uralensis,* 100 g of *Allium sativum,* 150 g of *Mentha canadensis,* 200 g of *Allium mongolicum,* 150 g of *Lonicera japonica,* 120 g of *Sargassum,* 35 g of calcium carbonate, 20 g of FOS, 12 g of IMO, and 40 g of organic selenium.

The preparation method of the enzyme in the comparative example 2 is as follows:

step 1, drying the *Lactuca sativa*, the *Allium tuberosum*, the *Litsea* rubescensLeeomte, the *Glycyrrhiza uralensis*, the *Allium mongolicum*, and the *Lonicera japonica* individually according to their weight to obtain dried materials, grinding the dried materials in a grinder to obtain grinded materials, decocting the grinded materials by using purified water to obtain decoction, and then filtering the decoction to obtain a slurry; soaking the *Artemisia argyi* and the *Mentha canadensis* into water for 1 h to obtain soaked materials, distilling the soaked materials by a steam distillation method to obtain a distilled product, and then adding the distilled product into water to perform a time of extraction by reducing pressure to obtain an extracted product, filtering and concentrating the extracted product to a target relative density, thereby obtaining a medicinal liquid 1 for later use; and crushing the *Allium sativum* and the *Allium cepiforme* to obtain crushed materials, adding the crushed materials into water to perform a warm infusion for 3 h in a hermetic environment to obtain an infused mixture, adding ethanol into the infused mixture until a concentration of the ethanol is 50%, thereafter performing an extraction by reducing pressure to obtain a product, filtering and concentrating the product to a target relative density, thereby obtaining a medicinal liquid 2;

step 2, adding the medicinal liquid 1, the medicinal liquid 2, and the slurry into a material mixing tank and then stirring evenly to obtain a mixed liquid;

step 3, adding the *Sargassum* into the mixed liquid obtained in the step 2, and stewing the mixed liquid added with the *Sargassum* to obtain a stewed product, taking out the stewed product to filter and cool down to obtain a cooled mixed liquid;

step 4, adding 20% of the weight of the FOS and 20% of the weight of the IMO into the cooled mixed liquid obtained in the step 3, and then stirring uniformly, and placing the cooled mixed liquid added with the FOS and the IMO into a fermentation tank for a first fermentation to obtain a first fermentation broth; taking out and filtering the first fermentation broth to obtain a filtered first fermentation broth, adding the remained FOS and the remained IMO into the filtered first fermentation broth, and then placing the filtered first fermentation broth added with the remained FOS and the remained IMO into the fermentation tank for a second fermentation to obtain a second fermentation broth;

step 5, crushing the calcium carbonate to obtain powder; placing the powder into a furnace with a temperature of 2,200° C. and then sintering for 75 min to obtain sintered powder; cooling the sintered powder to obtain cooled powder, placing the cooled powder into a cloth bag with 1,200 meshes and then distilling the cooled powder with a steamer to obtain a distilled liquid for later use; and step 6, distilling the second fermentation broth obtained in the step 4 until there is no distillate to obtain a distilled fermentation broth for later use; mixing the distilled fermentation broth, the distilled liquid obtained in the step 5, and the organic selenium completely to obtain a mixed liquid; adding the mixed liquid into olive oil according to a volume ratio of the mixed liquid to the olive oil of 1:10, thereby obtaining the enzyme.

Test Example 1

The enzymes obtained in the embodiments 1-2 and the comparative examples 1-2 are entrusted to Wuhan Institute of Virology to conduct experiments. The experiments are performed as follows: taking Vero E6 cells with a ratio of $1.5\times10^4$ cells/well to inoculate in a 48-well cell culture plate, respectively, and then culturing the 48-well cell culture plate in a 5% $CO_2$ incubator at 37° C. for 12-16 h; removing supernatant from the cells in the 48-well cell culture plate and incubating the cells for 1 h; adding SARS-coronavirus-2 into the cells at a biosafety level 3 (BSL-3) laboratory to infect the cells with a multiplicity of infection (referred to as a ratio of viruses to cells during infection and abbreviated as MOI) of 0.05; and then incubating the infected cells for 1 h, then removing supernatant thereof, washing the 48-well cell culture plate by using phosphate buffered saline (PBS), and adding the enzymes with different concentrations obtained from the embodiments or the comparative examples, and infecting the cells in the 48-well cell culture plate for 24 h to collect corresponding supernatant of the cells in the 48-well cell culture plate. 150 microliters (L) of the supernatant is charged from each well of the 48-well cell culture plate, and then the supernatant is added into 271 L of lysis solution to inactivate, thereby obtaining inactivated samples loaded in tubes; and then the tubes loaded with the inactivated samples are added with disinfectants, thereafter taking the tubes out of the BSL-3.

Table 1 illustrates an antibacterial effect of sample solution (i.e., the enzyme) obtained from the embodiment 1 on influenza A virus H1N1.

| Virus name | Action time | Experiment number | Air virus content (TCID50/m³) | Virus inactivation rate/% |
|---|---|---|---|---|
| Influenza A virus H1N1 Host name: Madin-Darby canine kidney (MDCK) cell | 0 (acting on canine kidney abbreviated as CK) | 1 | $3.24\times10^6$ | |
| | | 2 | $2.40\times10^6$ | |
| | | 3 | $3.24\times10^6$ | |
| | 2 h | 1 | $<1.62\times10^2$ | >99 |
| | | 2 | $<1.62\times10^2$ | >99 |
| | | 3 | $<1.62\times10^2$ | >99 |

Table 2 illustrates effects of products (i.e., the antiviral animal feed additive) prepared by the disclosure on influenza A virus H1N1.

| Experimental virus and host | Concentration and time of action | Group | Logarithmic value of virus titration lgTCID50/mL | Average total number of viruses lgTCID50/mL | Average total number of viruses after 24 h lgTCID50/mL | Virus inactivation rate/% |
|---|---|---|---|---|---|---|
| Influenza A virus H1N1 Host name: MDCK cell | Sample solution 24 h | Embodiment 1 | <1.5 | <1.5 | <31.6 | >99.99 |
| | | Embodiment 2 | <1.5 | | | |
| | | Comparative example 1 | 4.5 | 4.55 | $2.40\times10^5$ | |
| | | Comparative example 2 | 4.6 | | | |

Experimental conclusion: the products prepared by the disclosure are capable of killing over 99.99% of the influenza A virus H1N1 in the air. After the products are made into the sample solution, the killing rate of influenza A virus H1N1 is greater than 99.99%, indicating that the products obtained from the disclosure indeed have broad-spectrum antiviral effects.

Apparently, the above-mentioned embodiments are only used to clearly illustrate the disclosure, and are not intended to limit an implementation mode of the disclosure. The objective of the disclosure is to enable those skilled in the related art to understand the content of the disclosure and implement the disclosure according to the content, and the embodiments above cannot limit the scope of the protection of the disclosure. Any modification, equivalent replacement and improvement made within the spirit and principle of the disclosure shall fall within the scope of the protection of the disclosure.

What is claimed is:

1. A preparation method of an antiviral animal feed additive, comprising the following steps:

step 1, providing 300 g to 500 grams (g) of *Artemisia argyi,* 200 g to 300 g of *Lactuca sativa,* 200 g to 300 g of *Allium tuberosum,* 300 g to 400 g of *Allium cepiforme,* 200 g to 300 g of *Litsea rubescens* Leeomte, 50 g to 150 g of *Glycyrrhiza uralensis,* 50 g to 150 g of *Allium sativum,* 75 g to 150 g of *Mentha canadensis,* 100 g to 200 g of *Allium mongolicum,* 50 g to 150 g of *Lonicera japonica,* 80 g to 120 g of *Sargassum,* 20 g to 30 g of monazite, 25 g to 35 g of calcium carbonate, 10 g to 20 g of fructo-oligosaccharide (FOS), 8 g to 12 g of isomaltooligosaccharide (IMO), and 20 g to 40 g of organic selenium;

step 2, drying the *Lactuca sativa*, the *Allium tuberosum*, the *Litsea rubescens* Leeomte, the *Glycyrrhiza uralensis*, the *Allium mongolicum*, and the *Lonicera japonica* individually to obtain dried materials, grinding the dried materials in a grinder to obtain grinded materials, decocting the grinded materials by using purified water to obtain decoction, and then filtering the decoction to obtain a slurry; soaking the *Artemisia argyi* and the *Mentha canadensis* into water for 1 hour (h) to obtain soaked materials, performing steam distillation on the soaked materials to obtain a distilled product, and then adding the distilled product into water to perform a time of extraction by reducing pressure to obtain an extracted product, filtering and concentrating the extracted product to a target relative density, thereby obtaining a medicinal liquid 1; and crushing the *Allium sativum* and the *Allium cepiforme* to obtain crushed materials, adding the crushed materials into water for 3 h in a hermetic environment to obtain an infused mixture, adding ethanol into the infused mixture until a concentration of the ethanol is 50%, thereafter performing an extraction by reducing pressure to obtain a product, filtering and concentrating the product to a target relative density, thereby obtaining a medicinal liquid 2;

step 3, adding the medicinal liquid 1, the medicinal liquid 2, and the slurry into a material mixing tank and then stirring evenly to obtain a mixed liquid;

step 4, adding the *Sargassum* into the mixed liquid obtained in the step 3, and heating the mixed liquid added with the *Sargassum* to obtain a heated product, taking out the heated product to filter and cool down to obtain a cooled mixed liquid;

step 5, adding 20% of the weight of the FOS and 20% of the weight of the IMO into the cooled mixed liquid obtained in the step 4, and then stirring uniformly, and placing the cooled mixed liquid added with the FOS and the IMO into a fermentation tank for a first fermentation to obtain a first fermentation broth; taking out and filtering the first fermentation broth to obtain a filtered first fermentation broth, adding the remaining FOS and the remaining IMO into the filtered first fermentation broth, and then placing the filtered first fermentation broth added with the remaining FOS and the remaining IMO into the fermentation tank for a second fermentation to obtain a second fermentation broth;

step 6, crushing the monazite and the calcium carbonate to obtain mixed powder; placing the mixed powder into a furnace with a temperature of 2,000-2,200 degrees Celsius (° C.) and then sintering for 75-105 minutes (min) to obtain sintered powder; cooling the sintered powder to obtain cooled powder, placing the cooled powder into a cloth bag with 800-1,200 meshes and then distilling the cooled powder with a steamer to obtain a distilled liquid; and step 7, distilling the second fermentation broth obtained in the step 5 until there is no distillate to obtain a distilled fermentation broth; mixing the distilled fermentation broth, the distilled liquid obtained in the step 6, and the organic selenium completely to obtain a mixed liquid; adding the mixed liquid into olive oil according to a volume ratio of the mixed liquid to the olive oil of 1:5-10, thereby obtaining the antiviral animal feed additive;

wherein the organic selenium is in the form of one selected from the group consisting of selenium enriched yeast, kappa-selenocarrageenan, selenium enriched *Capsella bursa-pastoris* powder extract, selenium enriched *Cardamine occulta* powder extract, selenium enriched *Brassica rapa* powder extract, selenium enriched *Brassica oleracea* powder extract, and selenium enriched *Fructus Hordei germinatus* powder extract.

2. The preparation method as claimed in claim 1, wherein the step 1 comprises:

providing 300 g of the *Artemisia argyi,* 200 g of the *Lactuca sativa,* 200 g of the *Allium tuberosum,* 300 g of the *Allium cepiforme,* 200 g of the *Litsea rubescens* Leeomte, 50 g of the *Glycyrrhiza uralensis,* 50 g of the *Allium sativum,* 75 g of the *Mentha canadensis,* 100 g of the *Allium mongolicum,* 50 g of the *Lonicera japonica,* 80 g of the *Sargassum,* 20 g of the monazite, 25 g of the calcium carbonate, 10 g of the FOS, 8 g of the IMO, and 20 g of the organic selenium.

3. The preparation method as claimed in claim 2, wherein in the step 6, the temperature is 2,000° C., a time of the sintering is 105 min, and the cloth bag is 800 meshes.

4. The preparation method as claimed in claim 1, wherein the step 1 comprises:

providing 500 g of the *Artemisia argyi,* 300 g of the *Lactuca sativa,* 300 g of the *Allium tuberosum,* 400 g of the *Allium cepiforme,* 300 g of the *Litsea rubescens* Lecomte, 150 g of the *Glycyrrhiza uralensis,* 100 g of the *Allium sativum,* 150 g of the *Mentha canadensis,* 200 g of the *Allium mongolicum,* 150 g of the *Lonicera japonica,* 120 g of the *Sargassum,* 30 g of the monazite, 35 g of the calcium carbonate, 20 g of the FOS, 12 g of the IMO, and 40 g of the organic selenium.

5. The preparation method as claimed in claim 4, wherein in the step 6, the temperature is 2,200° C., a time of the sintering is 75 min, and the cloth bag is 1,200 meshes.

* * * * *